United States Patent
Goedicke et al.

(10) Patent No.: US 8,525,118 B2
(45) Date of Patent: Sep. 3, 2013

(54) CARDIAC SPECT SYSTEM WITH TRAJECTORY OPTIMIZATION

(75) Inventors: Andreas G. Goedicke, Aachen (DE); Herfried K. Wieczorek, Aachen (DE); Ralf Dorscheid, Kerkrade (NL); Michael Schaff, Herzogenrath (DE)

(73) Assignee: Koninklijke Philips N.V., Eindhoven (NL)

( * ) Notice: Subject to any disclaimer, the term of this patent is extended or adjusted under 35 U.S.C. 154(b) by 87 days.

(21) Appl. No.: 13/454,217

(22) Filed: Apr. 24, 2012

(65) Prior Publication Data
US 2012/0205542 A1 Aug. 16, 2012

Related U.S. Application Data

(62) Division of application No. 12/441,537, filed as application No. PCT/US2007/077978 on Sep. 10, 2007, now Pat. No. 8,183,532.

(60) Provisional application No. 60/826,462, filed on Sep. 21, 2006, provisional application No. 60/917,074, filed on May 10, 2007.

(51) Int. Cl.
*G01T 1/166* (2006.01)

(52) U.S. Cl.
USPC .................................................. 250/363.04

(58) Field of Classification Search
None
See application file for complete search history.

(56) References Cited

U.S. PATENT DOCUMENTS

| | | | |
|---|---|---|---|
| 4,503,331 A | 3/1985 | Kovacs, Jr. et al. | |
| 5,097,131 A | 3/1992 | Plummer et al. | |
| 5,565,684 A | 10/1996 | Gullberg et al. | |
| 5,598,003 A | 1/1997 | Jones et al. | |
| 5,777,332 A | 7/1998 | Lonn et al. | |
| 6,147,353 A | 11/2000 | Gagnon et al. | |
| 6,242,743 B1 | 6/2001 | DeVito et al. | |
| 6,288,397 B1 | 9/2001 | Maor | |
| 6,525,320 B1* | 2/2003 | Juni | 250/363.04 |
| 2002/0177773 A1* | 11/2002 | Natterer et al. | 600/436 |
| 2003/0136912 A1 | 7/2003 | Juni | |
| 2004/0263865 A1 | 12/2004 | Pawlak et al. | |
| 2006/0000983 A1 | 1/2006 | Charron et al. | |
| 2007/0080295 A1* | 4/2007 | Hamill | 250/363.03 |

FOREIGN PATENT DOCUMENTS
JP 2002006043 A 1/2002

OTHER PUBLICATIONS

Vandervoort, E., et al.; Implementation of an Analytically Based Scatter Correction in SPECT Reconstructions; 2005; IEEE Trans. on Nuclear Science; 52(3)645-653.

* cited by examiner

Primary Examiner — David Porta
Assistant Examiner — Edwin Gunberg

(57) ABSTRACT

In a disclosed imaging method, the instantaneous speed or data acquisition dwell times of a detector head is optimized as a function of position along a path of the detector head around a subject. The optimization is respective to an expected radioactive emission profile of a region of interest that is less than the entire subject. The detector head is traversed along the path using the optimized instantaneous speed or data acquisition dwell times. During the traversing, imaging data are acquired using the detector head. The acquired imaging data are reconstructed to generate a reconstructed image of at least the region of interest. A gamma camera configured to perform the foregoing imaging method is also disclosed.

11 Claims, 6 Drawing Sheets

CARDIAC SPECT SYSTEM WITH TRAJECTORY OPTIMIZATION

CROSS REFERENCE TO RELATED APPLICATIONS

Figure 1:
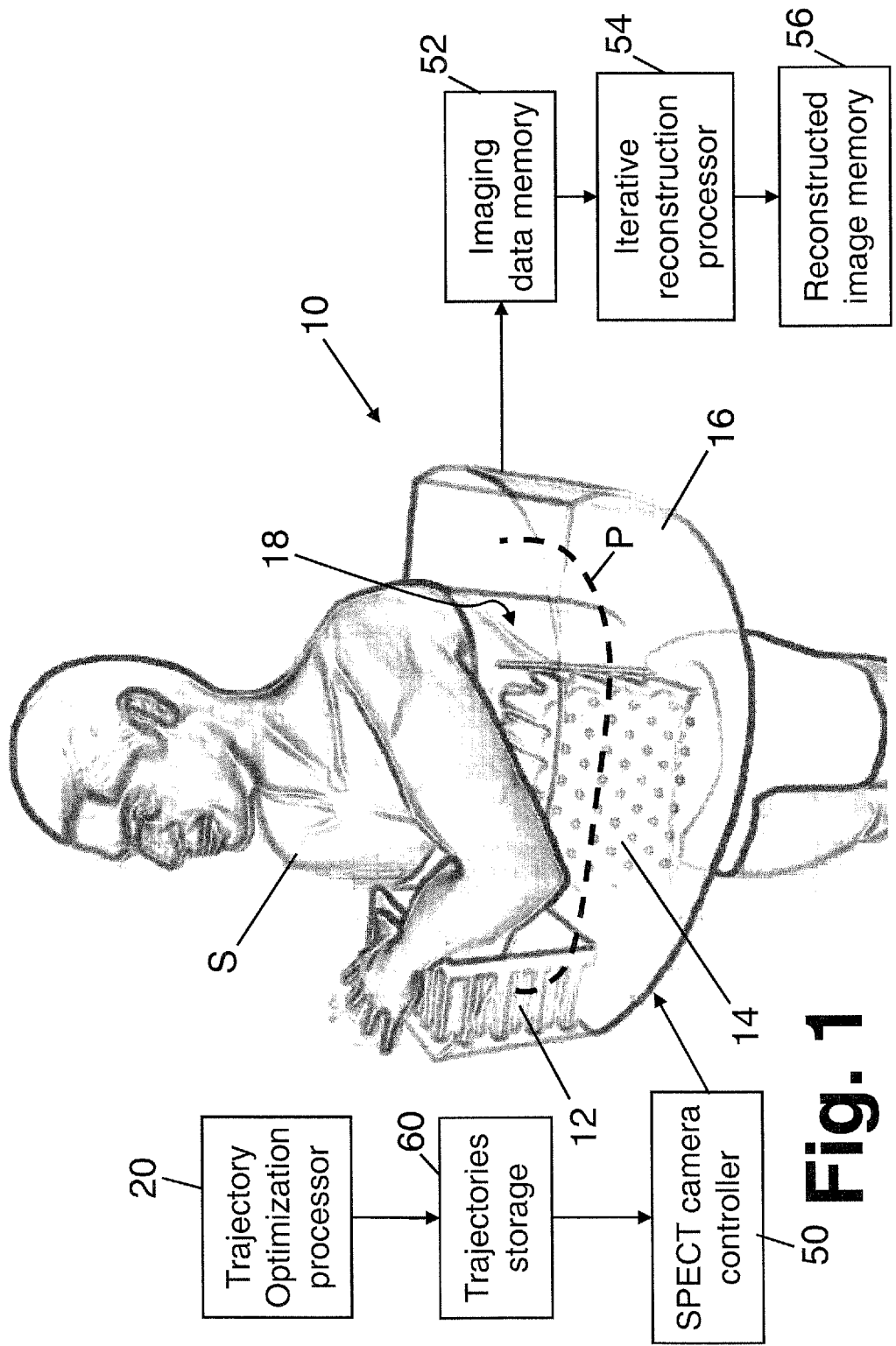

This application is a divisional application of U.S. patent application Ser. No. 12/441,537 filed Mar. 17, 2009 and issued May 22, 2012 as U.S. Pat. No. 8,183,532, which is a national filing of PCT application number PCT/US2007/077978 filed Sep. 10, 2007 which claims the benefit of U.S. provisional application Ser. No. 60/826,462 filed Sep. 21, 2006 and U.S. provisional application Ser. No. 60/917,074 filed May 10, 2007, all of which are incorporated herein by reference.

DESCRIPTION

The following relates to the imaging arts. It finds particular application in nuclear medical imaging and apparatuses for performing same. However, the following finds more general application in tomographic imaging methods and apparatuses generally.

In single-photon emission computed tomography (SPECT), one or more radiation detectors are arranged around a subject. A radiotracer previously administered to the subject (for example, a radiopharmaceutical previously administered to a human medical patient) generates radioactive emissions that are detected as radiation events or counts by the radiation detectors. The radiation event detections define imaging data that are reconstructed to generate an image generally indicative of the distribution of radiopharmaceutical in the subject. In some approaches, the radiopharmaceutical is selected to preferentially accumulate in an organ or other region of interest, such as the cardiac muscle for the purpose of cardiac imaging. The radiation detectors are typically arranged as a gamma camera with one or more radiation detector heads mounted on a gantry that enables tomographic movement of the heads around the subject so as to acquire views over an angular span of typically between about 180° and 360°, so as to facilitate reconstructing a three-dimensional image.

In a typical cardiac SPECT camera, two detector heads are positioned at a fixed 90° offset from one another on a circular or semi-circular gantry, and are revolved around the patient in unison at least about 90° so as to provide at least about 180° angular span of imaging data. The patient's torso is typically centered on an isocenter of rotation of the detector heads. This arrangement is convenient for scan setup, but it places the cardiac muscle in an offset position respective to the isocenter.

Reconstruction of SPECT imaging data to produce a three-dimensional image is a computationally complex process. In some approaches, a single-pass filtered backprojection reconstruction is used. This approach is relatively fast, and is deterministic in nature. However, single-pass filtered backprojection is susceptible to generating image artifacts caused by noise in the image data. Iterative statistical methods such as maximum likelihood-expectation maximization (ML-EM) have also been developed. These techniques are non-deterministic, i.e., statistical in nature, and are substantially slower and more computationally intensive than filtered backprojection. However, statistical techniques such as ML-EM have improved robustness against noise as compared with filtered backprojection.

To address the slow convergence of ML-EM, an accelerated derivative technique known as ordered subset-expectation maximization (OS-EM) has been developed. OS-EM is also an iterative process, but operates by processing selected sub-sets of the imaging dataset. Instead of computing an estimate update after all projections have been evaluated (as in the ML-EM approach), in the OS-EM approach the projections are grouped in appropriate sub-sets and estimation updates are computed after evaluating each of the subsets.

Processing subsets of the data substantially enhances convergence speed, but introduces certain disadvantages. For example, the convergence speed and accuracy of OS-EM depends on the detailed projection subset arrangement or selection, and on the total information about the object contained in each subset of projection data. While ML-EM generally provides ensured convergence given sufficient number of iterations, OS-EM and related techniques that process subsets of data are ensured to converge only if a criterion known as the subset balance criterion is fulfilled. Stated in a simplified manner, the subset balance criterion calls for each projection subset to contain the same amount of information about the observed tracer distribution. If the subset balance criterion is not satisfied, which is typical in clinical applications, then the OS-EM reconstruction is known to converge to the so-called limit-cycle, given by a finite number of distinct positions in the solution space. A consequence of this is that the decision as to which subset is evaluated last has an impact on the final reconstruction result. In practice, iterative SPECT reconstruction algorithms are typically stopped before limit-cycles occur, because iterating until a limit-cycle is reached tends to produce non-physical, noisy results. Even with early termination, however, the quality of the reconstructed image is dependent on the choice of projection subsets and their processing order when the subset balance criterion is not met or well-approximated.

In accordance with one aspect, an imaging method is disclosed. The instantaneous speed or data acquisition dwell time of a detector head is optimized as a function of position along a path of the detector head around a subject. The optimization is respective to an expected radioactive emission profile of a region of interest that is less than the entire subject. The detector head is traversed along the path using the optimized instantaneous speed or data acquisition dwell times. During the traversing, imaging data are acquired using the detector head. The acquired imaging data are reconstructed to generate a reconstructed image of at least the region of interest.

In accordance with another aspect, a gamma camera configured to perform the method of the preceding paragraph is disclosed.

In accordance with another aspect, a gamma camera is disclosed, including one or more detector heads and a gantry configured to move the one or more detector heads along a detector head path at controllable variable speed or controllable data acquisition dwell times.

In accordance with another aspect, an imaging method is disclosed. A plurality of detector heads are concurrently traversed around a subject spaced apart along a path and moving at different instantaneous speeds or with different data acquisition dwell times. During the traversing, imaging data are acquired using the plurality of detector heads. The acquired imaging data are reconstructed to generate a reconstructed image of at least a region of interest of the subject.

In accordance with another aspect, a lookup table is disclosed. The lookup table contains optimized detector head trajectory data comprising one of optimized detector head speed and optimized data acquisition dwell times for a radiation detector head traversing a selected path and acquiring imaging data from a region of interest of a subject.

In accordance with another aspect, a gamma camera is disclosed, comprising at least one detector head disposed in a gantry and passive constraints that constrain the at least one detector head to move along a path in or on the gantry with a radiation sensitive face of the at least one detector head facing toward a region of interest.

One advantage resides in more rapid iterative image reconstruction.

Another advantage resides in more accurate iterative image reconstruction.

Another advantage resides in providing a cardiac SPECT camera that is more comfortable for patients.

Another advantage resides in providing an improved cardiac SPECT camera.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 shows a perspective view of a cardiac SPECT camera arranged for cardiac imaging of a human subject. In FIG. 1, a stationary gantry of the SPECT camera is shown in a translucent manner to reveal internal components including two radiation detector heads.

Figure 2:
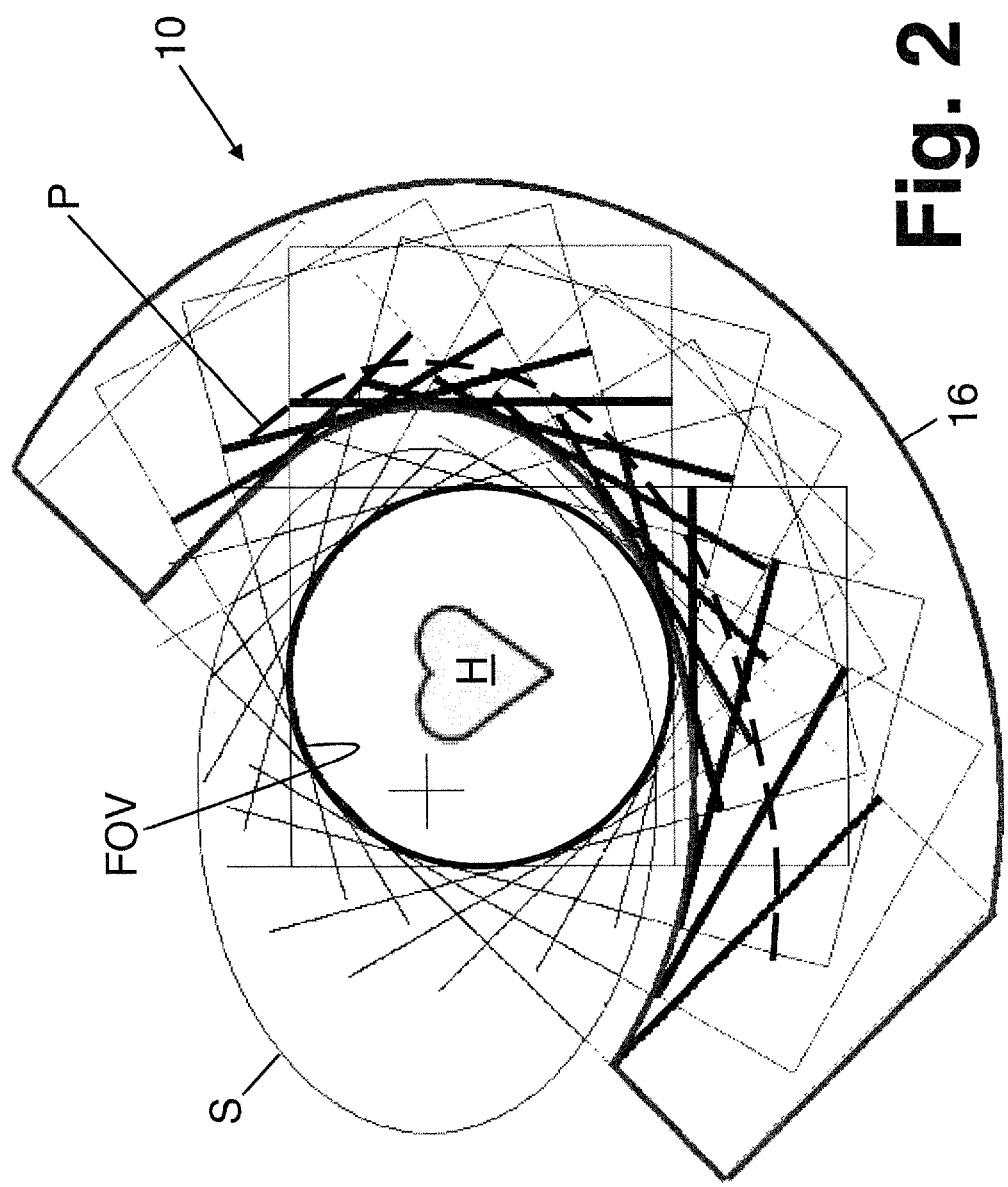

FIG. 2 diagrammatically shows an axial slice passing through the SPECT camera and the torso of the subject of FIG. 1.

Figure 3B:
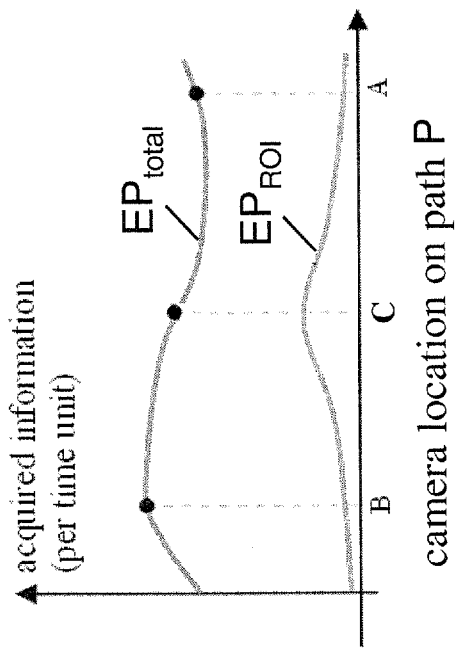
Figure 3A:
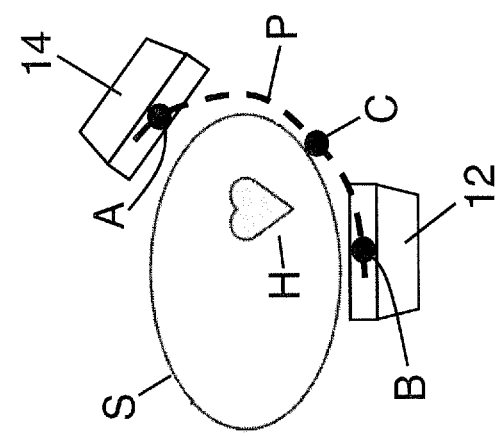

FIG. 3A diagrammatically identifies example positions "A", "B", and "C" of detector heads along a path.

FIG. 3B plots radioactive emission profiles for the subject and for the cardiac region of interest.

Figure 4:
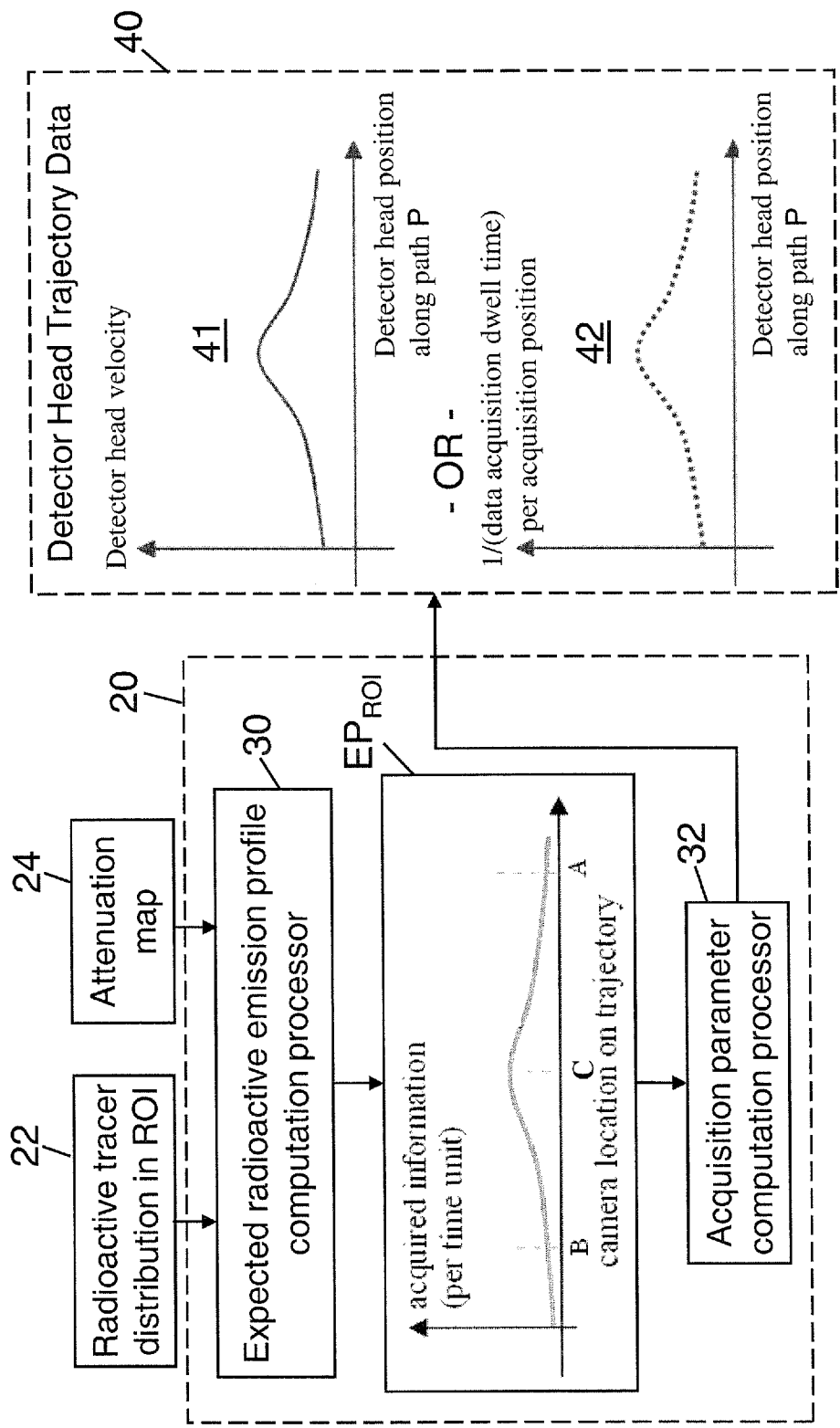

FIG. 4 diagrammatically shows a system for optimizing trajectories of radiation detector heads.

Figure 5:
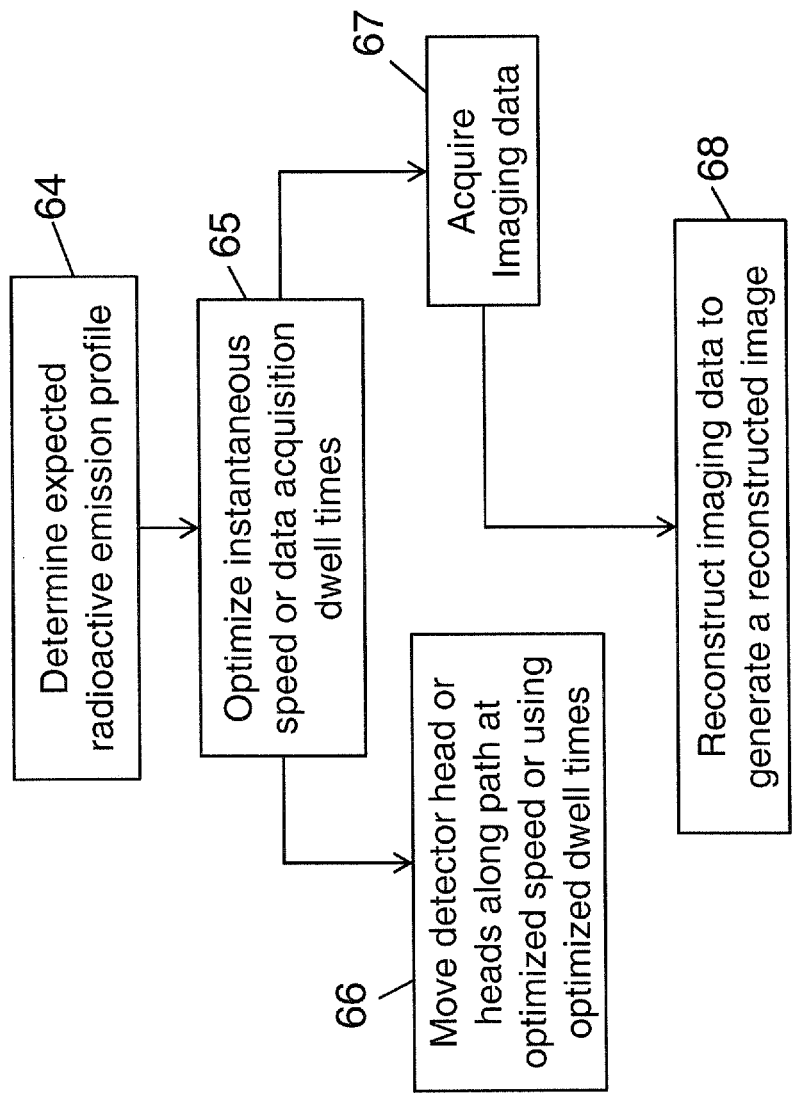

FIG. 5 diagrammatically shows an imaging method suitably practiced using the camera of FIGS. 1 and 2.

Figure 6:
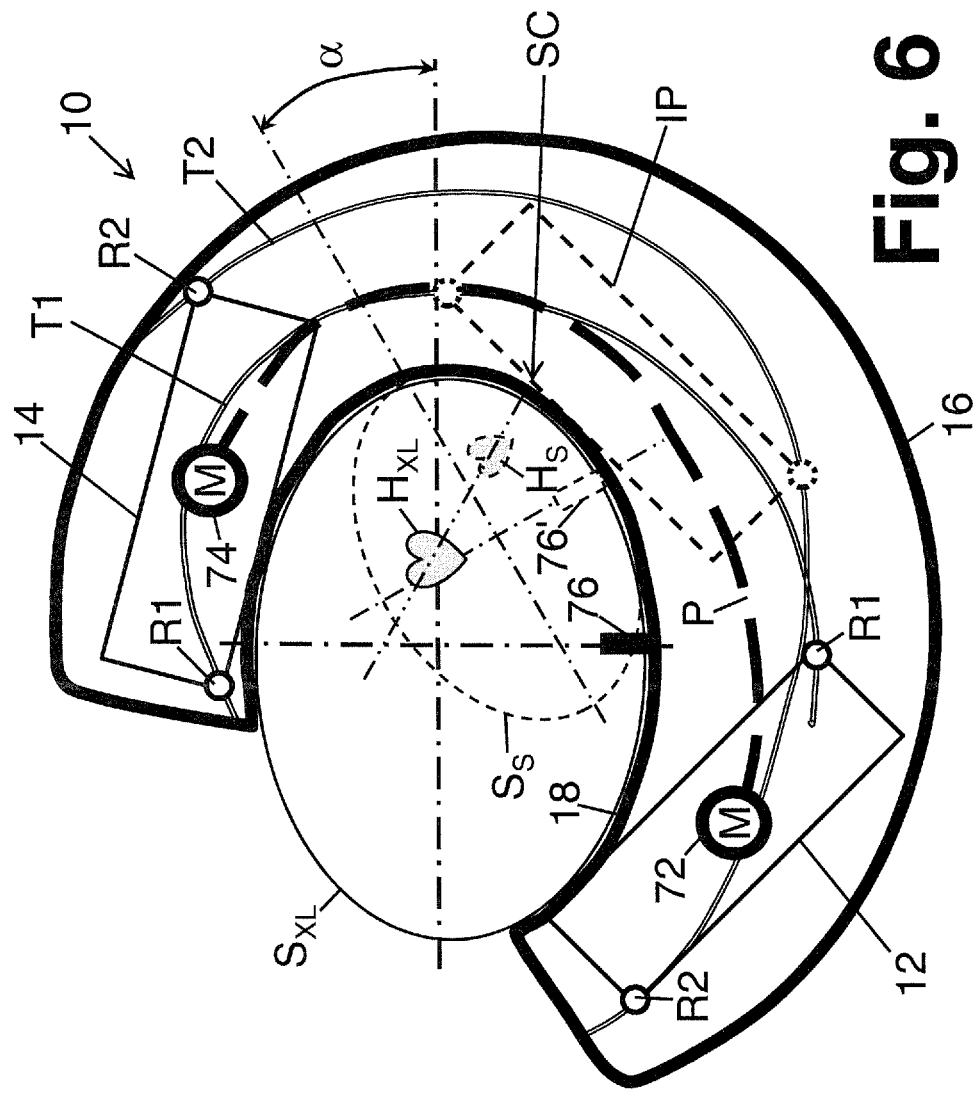

FIG. 6 diagrammatically shows how the SPECT camera of FIGS. 1 and 2 can accommodate subjects of different sizes using a fixed path for the radiation detector heads.

With reference to FIG. 1, a gamma camera such as an illustrated cardiac SPECT camera 10 includes one or more detector heads, such as an illustrated two detector heads 12, 14, disposed on or in a gantry 16. Each detector head 12, 14 employs a suitable radiation detector array, such as for example a photomultiplier tube array, a diode detector array, an array of NaI crystal detectors, or so forth. Suitable collimation is provided to define projection data, for example using a radiation-absorbing honeycomb collimator disposed in front of the detector array. The illustrated gantry 16 includes an exterior elliptical wall 18 substantially conforming with an elliptical path P (indicated by a dashed line in FIG. 1) of the detector heads 12, 14, and also substantially conforming with a torso of a human subject S. More generally, the path P is a known path, which in the illustrated embodiment is generally elliptical to substantially conform with the shape of the torso. For other subjects or subject portions, a non-elliptical path may be preferable. For example, if the region of interest is the prostate, then an non-elliptical path close to the groin may be advantageous. Moreover, it is contemplated for the path P to be adjustable for patients of different sizes, for example by adding or removing expansion joints. For two optionally inserted expansion joints, for example, there are four selectable paths P corresponding to no expansion joints inserted, both expansion joints inserted, and two additional paths selected by inserting a selected one of the two expansion joints.

During imaging, the one or more detector heads 12, 14 move along the path P and acquire imaging data. In some embodiments, the detector heads move continuously while acquiring data. In some embodiments, the detector heads move in a "step-and-shoot" configuration in which the head moves to an acquisition position, acquires data, and then moves to the next acquisition position, and so forth, acquiring imaging data only when the head is stationary in an acquisition position. In some embodiments, the detector heads 12, 14 may move relatively fast and traverse the path P several times in a back-and-forth fashion while acquiring imaging data. Typically, a continuous data acquisition mode is advantageous when the heads are swept back-and-forth to acquire data. It is to be understood that the trajectory of a head may be either a continuous trajectory in which the instantaneous velocity at each point along the path P is specified, or a step-and-shoot trajectory in which the dwell time of the detector head at each acquisition position is specified. Moreover, it is to be understood that the trajectory may be either a single-pass trajectory in which the detector head moves in a single pass along some or all of the path P, or may be a back-and-forth trajectory in which the detector head moves back-and-forth in two or more passes along some or all of the path P. It is also contemplated for the trajectory to be a multiple-pass trajectory in which the detector head rewinds back to the same starting position along the path P for each pass, so that the detector head moves along the same direction during data acquisition for multiple passes.

The gantry 16 is configured to provide positioning of the detector heads 12, 14 close to the torso of the human subject S, and provides an apparently static gantry as observed by the subject S. The movement of the detector heads 12, 14 inside the gantry 16 is not readily apparent to the subject S, except perhaps indirectly through vibration or noise. The stationary gantry 16 optionally serves as an armrest or table for the subject S. In some embodiments, the conformal exterior wall 18 is relatively thin and in direct contact with the subject S, and the detector heads are in contact with, or spaced apart by a small tolerance from, the interior side of the wall 18, which enables the detector heads 12, 14 to be close to the subject 18 throughout their movement along the path P. About 30% higher efficiency is achievable with such a direct contact arrangement as compared with detector heads arranged at a two centimeter distance from the subject S.

With reference to FIG. 2, an axial slice is diagrammatically shown passing through the SPECT camera 10 and the torso of the subject S. A position of a cardiac muscle H in the subject S is diagrammatically indicated in FIG. 2 using a "heart" symbol. For cardiac imaging, the cardiac muscle H is the region of interest. In other clinical or diagnostic applications, another organ or tissue may be the region of interest, such as the prostate. The radiopharmaceutical is typically selected to preferentially accumulate in the organ or tissue of interest. The path P followed by the detector heads 12, 14 is generally centered on the heart H, although some deviation from a central positioning of the heart is contemplated. A locus of field-of-view edge lines for various acquisition positions of the detector heads 12, 14 along the path P are indicated in FIG. 2. The field-of-view edge lines for each position are substantially perpendicular to the face of the detector head due to the typical use of linear or small-angle conical collimators in the detector heads 12, 14. As indicated in FIG. 2, the locus of field-of-view edge lines collectively define a generally circular or elliptical field-of-view boundary FOV that is generally centered on the heart H positioned at about the isocenter of the path P and positioned asymmetrically with respect to the torso of the subject S.

With reference to FIGS. 3A and 3B, radioactive emission characteristics observed by the detector heads 12, 14 along the path P are illustrated. FIG. 3A diagrammatically shows an axial slice passing through the detector heads 12, 14 and the subject S including the heart H. In FIG. 3A, the gantry 16 is omitted for clarity. At the point in time illustrated in FIG. 3A, the detector head 14 is at a position denoted "A" while the detector head 12 is at a position denoted "B". An additional position "C" intermediate between the positions "A" and "B" is also labeled. FIG. 3B plots the expected total information acquired from the total subject S per unit time along the path P, that is, the radioactive emission profile $EP_{total}$, and also plots the acquired information from the region of interest H per unit time along the path P (that is, the radioactive emission profile $EP_{ROI}$). The total emission profile $EP_{total}$ and the emission profile $EP_{ROI}$ from the heart H are different in magnitude and shape or form. For example, at the position "B" the total emission profile $EP_{total}$ has a high value respective to other positions along the path P, whereas the radioactive emission profile $EP_{ROI}$ from the heart H is relatively low at position "B". In contrast, at the position "C", the total emission profile $EP_{total}$ is relatively lower, whereas the region of interest emission profile $EP_{ROI}$ is at its peak at position "C". The different shapes of the total radioactive emission profile $EP_{total}$ and the region of interest emission profile $EP_{ROI}$ reflects differentiating factors such as the detector-to-torso versus detector-to-heart distance, the distribution of intervening radiation-absorbing tissue such as bone, the angle of the line-of-sight of the detector head respective to the torso or heart, and so forth.

To accommodate the non-constant radioactive emission profile $EP_{ROI}$ of the region of interest (that is, the heart H in the example case of cardiac imaging), the trajectory of each SPECT camera 10 is independently configured such that each detector head 12, 14 moves independently along the path P to optimize the data acquisition respective to the region-of-interest emission profile $EP_{ROI}$ so as to facilitate satisfying or substantially satisfying the subset balance criterion. By optimizing or balancing the information distribution in the acquired imaging data, the subset balance criterion is more readily satisfied or approximated during iterative reconstruction, which in turn results in iterative reconstruction that is faster and more accurate.

The trajectories are optimized by optimizing the instantaneous speed or data acquisition dwell times of each detector head as a function of position along the path P respective to the radioactive emission profile $EP_{ROI}$ of the region of interest H, which is less than the entire subject S. The instantaneous speed or data acquisition dwell times of each detector head are optimized with respect to the region of interest radioactive emission profile $EP_{ROI}$ rather than with respect to the total emission profile $EP_{total}$, because it is desired to optimize the reconstructed image in the region of interest. In each optimized trajectory, the detector head moves relatively more slowly (in the case of continuous data acquisition) or has relatively longer data acquisition dwell times (in the case of discrete step-and-shoot imaging) in those portions of the path P for which the radioactive emission profile $EP_{ROI}$ from the region of interest H is low. In contrast, the detector head moves relatively faster or has relatively shorter data acquisition dwell times in those portions of the path P for which the radioactive emission profile $EP_{ROI}$ from the region of interest H is high. The objective of the trajectory optimization is to achieve substantially the same expected count of radioactive events from the region of interest H for each angular interval or data acquisition dwell time along the path P. It is to be understood that the term "optimization" and "optimize" as used herein is to be broadly construed as encompassing non-global or approximate optimization of the trajectories respective to the radioactive emission profile $EP_{ROI}$ from the region of interest H. For example, an iterative optimization may be applied that is terminated when the expected count of radioactive events for each angular interval or data acquisition dwell time is uniform to within a specified measure.

With reference to FIG. 4, a suitable system 20 for optimizing the trajectories of the detector heads 12, 14 is described. The system 20 receives as input a radioactive tracer distribution 22 in the region of interest H of the subject S. Optionally, the system 20 further receives as input additional information such as an attenuation map 24 derived from transmission computed tomography (CT) imaging data or another source. Based on these sources of information, an expected radioactive emission profile computation processor 30 estimates or computes the expected radioactive emission profile $EP_{ROI}$ of the region of interest H of the subject S. An acquisition parameter computation processor 32 computes suitable detector head trajectory data 40 for each detector head 12, 14 based on the expected radioactive emission profile $EP_{ROI}$ of the region of interest H. For example, the acquisition parameter computation processor 32 computes the trajectory 41 as detector head speed as a function of position along the path P in the case of continuous acquisition, or as detector head position dwell time per acquisition position for step-and-acquire imaging.

The radioactive tracer distribution 22 can be obtained in various ways, such as from similar, earlier examinations, or from theoretical computations. The attenuation map 24 or other structural information can be obtained from CT imaging, from a line/point-source scan in conjunction with the expected or typical radioactive tracer distribution 22, or so forth. If the absorption information 24 is unavailable, the trajectory optimization is suitably performed using an estimated object outline, for example assuming that the object is homogeneously filled with water or another suitable material.

For a given detector head and a given acquisition position along the path P of that detector head, an estimate $EP_{ROI}$ of the radioactive emission rate is made based on the radioactive tracer distribution 22 and the absorption information 24. The optimized detector head speed 41 or data acquisition dwell times 42 are selected so as to spend more acquisition time at those trajectory locations where the amount of information acquired per time unit is low, and less time elsewhere. In the example SPECT camera 10 of FIGS. 1 and 2, there are two detector heads 12, 14 configured to be scanned independently. In such a case where there are multiple detector heads that can be independently scanned, the trajectory optimization system 20 is suitably applied to each detector head independently, except that it is advantageous to constrain the optimizations to ensure that detector head collisions are avoided.

With continuing reference to FIG. 4 and with further reference back to FIG. 1, in some embodiments the detector head trajectory data 40 is computed by the trajectory optimization system 20 before commencement of the imaging data acquisition. The pre-computed detector head trajectory data 40 are used by a controller 50 to control the SPECT camera 10 to perform a single-pass data acquisition in which the detector head or heads 12, 14 traverse the path P using the computed trajectories 40 and, during the traversing, imaging data are acquired using the detector head or heads 12, 14. The acquired imaging data are stored in a memory 52, and are reconstructed by an iterative reconstruction processor 54 implementing an iterative reconstruction algorithm that processes sub-sets of data, such as an ordered sub-set expectation maximization (OS-EM) algorithm. Because the optimized pre-computed detector head trajectory data 40 is used during imaging data acquisition, the sub-sets of imaging data typically satisfy or substantially satisfy the subset balance criterion so that iterative reconstruction speed and accuracy are enhanced. The reconstruction processor 54 generates a reconstructed image of at least the region of interest that is stored in an images memory 56. The reconstructed image can be displayed, processed, manipulated, communicated via a hospital network or the Internet, or otherwise utilized.

If multiple detector heads 12, 14 are used, then a collective dataset is formed that combines the acquired imaging data from the plurality of detector heads 12, 14. The collective dataset is reconstructed by the reconstruction processor 54 using an iterative reconstruction algorithm such as an OS-EM that iteratively processes selected sub-sets of the collective dataset to generate the reconstructed image.

In other embodiments, a two-pass data acquisition is used in which the traversing and the acquiring are performed as an integrated process. In a first imaging data acquisition pass, the detector head or heads 12, 14 are traversed around the subject S along the path P using non-optimized (or partially optimized) trajectory with non-optimized (or partially optimized) instantaneous speed or data acquisition dwell times, and first imaging data are acquired during the first traversing using the detector head or heads 12, 14. The first trajectory may, for example, employ a non-optimized constant instantaneous detector head speed or constant data acquisition dwell times, or partially optimized speed or dwell times based on previous imaging of similar patients. The resulting first imaging data are used to determine the expected radioactive emission profile $EP_{ROI}$ of the region of interest H, for example by performing an approximate reconstruction of the first imaging data using a fast approximate reconstruction algorithm such as filtered backprojection. Based on the expected emission profile $EP_{ROI}$, the acquisition parameter computation processor 32 determines one or more angular intervals over which the first imaging data are deficient. In a second imaging data acquisition pass, the detector head or heads 12, 14 are traversed along at least that portion of the path P including the one or more angular intervals over which the first imaging data are deficient using optimized instantaneous speed or data acquisition dwell times 40 computed by the acquisition parameter computation processor 32 using the expected emission profile $EP_{ROI}$ derived from the first imaging data as input. During the second traversing, completing imaging data are acquired over at least the one or more angular intervals over which the first imaging data are deficient. This forms a suitable collective imaging dataset that satisfies or substantially satisfies the subset balance criterion respective to the region of interest H that is suitable for reconstruction by the OS-EM reconstruction algorithm or another iterative reconstruction algorithm that processes subsets of imaging data.

In another approach, a first pass acquires scout imaging data that is not used in the image reconstruction, but which is approximately reconstructed by filtered backprojection or the like to generate the expected radioactive emission profile $EP_{ROI}$ of the region of interest H. The expected radioactive emission profile $EP_{ROI}$ generated from the scout data is input to the acquisition parameter computation processor 32 to generate optimized instantaneous speed or data acquisition dwell times 40. A second pass is then performed using the optimized instantaneous speed or data acquisition dwell times 40 to acquire the imaging data that are used for clinical or diagnostic image reconstruction, while the scout data are discarded.

In some embodiments, it is contemplated to adjust the instantaneous speed or data acquisition dwell times during the traversing and imaging data acquisition based on differences between the acquired imaging data and expected imaging data estimated from the expected radioactive emission profile $EP_{ROI}$ of the region of interest H of the subject S.

In some embodiments, the trajectory data 40, e.g. the optimized instantaneous speed 41 or data acquisition dwell time values 42, are retrieved from a data storage 60. The optimized instantaneous speed 41 or data acquisition dwell time values 42 may, for example, be stored in the data storage 60 as a lookup table. In such embodiments, the retrieved optimized trajectory data 40 are pre-determined to be optimized respective to the expected radioactive emission profile $EP_{ROI}$ of the region of interest H. In some such embodiments, the optimizing includes determining a dimension of the region of interest, and selecting the optimized instantaneous speed or data acquisition dwell time values for retrieval based on the determined dimension. For example, trajectories appropriate for different expected radioactive emission profiles for different sized hearts can be stored in the trajectories storage 60. The size, weight, or other dimension of the heart of a patient about to be imaged is then estimated from the size, weight or other characteristic of the patient, and the appropriate trajectories retrieved. The stored trajectories information in such embodiments can be locally stored, or can be from a regional or national database that is accessed via the Internet or another digital network. Rather than storing the optimized instantaneous speed or dwell times, in some embodiments the expected radioactive emission profile $EP_{ROI}$ of the region of interest is stored, and is input to the trajectories optimization processor 20 prior to imaging to generate the trajectories.

In the illustrated SPECT camera 10, both detector heads 12, 14 follow the same path P, although each detector head may traverse a different portion of the path P during the imaging. In other embodiments, it is contemplated to have detector heads that traverse different paths during the imaging. Moreover, while two detector heads 12, 14 are illustrated, in other embodiments one, three, or more detector heads may be included.

With reference to FIG. 5, a block diagram of a suitable imaging sequence is set forth. The expected radioactive emission profile $EP_{ROI}$ of the region of interest is determined in operation 64. This can be done in various ways. For example, in some embodiments this profile is determined for the subject to be imaged using a scout scan. In other embodiments this profile is retrieved from the lookup table or other data storage 60, for example retrieving the standard profile for the subject size closest to the size of the subject to be imaged. Based on the expected radioactive emission profile $EP_{ROI}$, the instantaneous speed or data acquisition dwell times for moving the one or more detector heads 12, 14 along the path P are determined in operation 65. In some embodiments, operations 64, 65 may be combined in that standard trajectories along the path P are determined based on the expected radioactive emission profile $EP_{ROI}$ and stored in the storage 60. The detector head or heads 12, 14 are moved along path P at the determined optimized speed or speeds, or using the optimized dwell times, in operation 66. Concurrently with the moving, the detector head or heads 12, 14 acquire imaging data in concurrent operation 67. The acquired imaging data are reconstructed into a reconstructed image of at least the region of interest in operation 68.

FIGS. 1 and 2 show the SPECT camera 10 imaging the subject S whose torso is large enough to substantially fill the examination region of the gantry and conform with most of the conformal exterior wall 18. In practice, subjects come in a variety of difference sizes, from petite, thin persons to large, obese persons.

With reference to FIG. 6, it is shown that the camera 10 can accommodate a range of different subject sizes while employing a single path P for the radiation detector heads 12, 14. In FIG. 6, the radiation detector head 12 is shown at its extreme clockwise position, while the radiation detector head 14 is shown at its extreme counterclockwise position. An illustrative intermediate detector head position IP is also shown in phantom, which may be occupied by either radiation detector head 12, 14 depending upon the time and trajectory. In the configuration of FIG. 6, the gantry 16, and particularly the conformal exterior wall 18 facing the examination region, are sized and shaped to just accommodate an extra-large subject $S_{XL}$. For such a subject, the radiation detector heads move their full range along the path P during imaging to acquire imaging data over a sufficiently large angular range to image the extra-large subject $S_{XL}$.

On the other hand, the small subject $S_S$ does not fill the examination region of the camera 10. Instead, the small subject $S_S$ is positioned as close as feasible, for example in contact with, a central portion of the conformal exterior wall 18 of the camera 10, as shown in FIG. 6. Rotating the torso of the small subject $S_S$ by an angle α as compared with the large subject $S_{XL}$ enables a larger portion of the small subject $S_S$ to contact or be in close proximity with the conformal exterior wall 18. The precise value of the angle α depends upon the size and shape of the subject's torso. By positioning the small subject $S_S$ as close as feasible to the conformal exterior wall 18 of the gantry 16, it is ensured that the detector heads 12, 14 are close to the small subject $S_S$, enabling intrinsic optimization of SPECT image quality.

Additionally, the placement of the small subject $S_S$ close to the central portion of the conformal exterior wall 18 with the angular rotation α ensures that a center of the region of interest of the small subject $S_S$ (such as the illustrated heart $H_S$ of the small subject $S_S$) and a center of the region of interest of the extra-large subject $S_{XL}$ (such as the illustrated heart $H_{XL}$ of the extra-large subject $S_{XL}$) both have the same scan center SC along the path P. As seen in FIG. 6, both region of interest centers $H_S$, $H_{XL}$ are roughly centered in the examination region of the gantry 16 and have a closest approach to the conformal exterior wall 18 at about the same scan center SC.

The path P is optimized for imaging the region of interest having the center $H_{XL}$. The path P is not as optimal for imaging the region of interest having the center $H_S$, but this is compensated by the positioning of the center $H_S$ closer to the radiation detectors 12, 14. The detector heads 12, 14 move along the same path P during imaging of the small subject $S_S$ as they do during imaging of the extra-large subject $S_{XL}$. However, the detector heads 12, 14 optionally move a smaller range along the path P during imaging of the small subject $S_S$ as compared with imaging of the extra-large subject $S_{XL}$. The smaller angular range is centered at about the scan center SC. More generally, the angular range is suitably adapted for subjects of different size, with the angular range in each size centered at about the same scan center SC. In other embodiments, a 180° range or larger range is covered regardless of patient size.

Some typical dimensions for the torso of the extra-large subject $S_{XL}$ may be, for example, 46 cm×32 cm, while typical dimensions for the torso of the small subject $S_S$ may be, for example, 30 cm×20 cm. These are merely examples, and the size and aspect ratio range should comport with the range of typical girths for the population of interest.

In one suitable mechanical construction, the centers of the two detector heads 12, 14 move along the path P during imaging along an angular range (which is generally different for each detector head 12, 14) selected based on the subject size. The motion of the detector heads is constrained to follow the path P by a first passive constraint defined by a first extended camming surface, groove, or other guide or track T1 guiding a first ball bearing, cam, roller, or other coupling R1 at one corner of each detector head 12, 14, and by a second passive constraint defined by a second extended camming surface, groove, or other guide or track T2 guiding a second ball bearing, cam, roller, or other coupling R2 at the opposite corner of each detector head 14. The curvatures of the constraint tracks T1, T2 are selected to keep the centers of the radiation detectors 12, 14 along the path P and the radiation-sensitive faces of the detector heads 12, 14 facing the position of the center of the largest region of interest (that is, facing the heart $H_{XL}$ of the extra-large subject $S_{XL}$). For the small subject $S_S$, the direction of the radiation-sensitive faces of the detector heads 12, 14 will deviate slightly from the heart $H_S$ due to the positional offset of the heart $H_S$ respective to the heart $H_{XL}$. However, this is compensated by the closer position of the detector faces to the heart $H_S$. Moreover, the deviation increases with angular position away from the scan center SC, and so if a smaller angular range is used for imaging the smaller subject $S_S$, this further reduces the effect of the directional deviation. Alternatively, a 180° range or larger range may be covered regardless of patient size.

The constraints R1, R2, T1, T2 can take various mechanical forms. For example, the camming surfaces or tracks T1, T2 can be machined curved tracks, grooves, surfaces, or the like in the gantry 16 manufactured by casting, milling, grinding, or another process, or using an existing profiled material that is recast into suitable path-defining shapes. In some embodiments, an inside wall of the gantry 16 corresponding to the conformal exterior wall 18 serves as a camming surface or track that constrains the movement of the detector heads 12, 14.

By using passive constraints R1, R2, T1, T2 in which the motion of each detector head 12, 14 is passively constrained (as opposed to being defined using active actuators, robotic arms, or the like) a single respective motor 72, 74 per detector head 12, 14 is sufficient to independently drive the two radiation detector heads 12, 14 along the path P with the radiation-sensitive faces continually viewing the center of the largest accepted region of interest $H_{XL}$. For mechanical accuracy it is advantageous to have the detector heads 12, 14 move only in one direction (either clockwise or counterclockwise) along the path P during image acquisition. However, bi-directional, e.g. back-and-forth, movement is also contemplated. By providing a separate drive motor 72, 74 for each detector head 12, 14, both heads 12, 14 can be moved independently along the same path P. The positions of the detector heads 12, 14 moving along the path P can be determined by sensors along the tracks T1, T2 that detect passage of the couplings R1, R2, or by a travel sensor built into the driving motors 72, 74, or so forth. Moreover, although passive constraints such as the illustrated passive constraints R1, R2, T1, T2 have certain advantages including at least those set forth herein, it is also contemplated to employ active detector head robotics, actuators, or so forth to provide independent movement for one, two, or more radiation detector heads, optionally including movement of detector heads toward or away from the subject.

Any suitable approach can be used to define the angular range for image scanning. In some embodiments, an element is used to determine the subject size. For example, the element can be a tape measure (not shown) used to measure the subject's waist size prior to the subject's entering the examination region, and the angular range is selected from a look-up table or function relating waist size with angular range. In another contemplated approach, the element is a handle 76 slidably mounted in a horizontal groove or slot formed into the conformal exterior wall 18. The handle 76 is held by the subject with both hands to define the angular orientation α of the subject. The angular range is then determined from the angular orientation α. For example, the handle 76 is shown where the extra-large subject $S_{XL}$ would hold it centered in front, whereas the phantom handle 76' shows where the small subject $S_S$ would hold the handle. Other elements can be used to determine subject size from a measured parameter—for example, the element can be a weight scale and the subject size can be inferred from a measured subject weight. If an initial scout scan is used to generate an expected radioactive emission profile $EP_{ROI}$ of the region of interest H for optimizing the imaging data acquisition, then the initial scout scan optionally can also be used to size the patient and identify the size and position of the heart $H_S$ or heart $H_{XL}$.

By having the movement of the detector heads 12, 14 constrained by the passive constraints R1, R2, T1, T2 in combination with positioning the subject, regardless of size, as close as possible to the scan center SC, there is no call for robotic arms, actuators, expansion joints, or other mechanically complex features for adapting the system to different patient sizes. A single motor 72, 74 per detector head 12, 14 is generally sufficient to drive a given radiation detector head along the constrained path, although two or more motors or motive devices are contemplated to provide smoother motion. While motors 72, 74 mounted in respective detector heads 12, 14 are diagrammatically illustrated, other motive devices can be used, such as a motor for each detector head mounted stationary in the gantry 16 and operatively coupled with the respective detector head by a drive chain, drive belt, or other mechanical coupling. In the illustrated embodiment, the detector heads 12, 14 move horizontally so the motors 72, 74 or other motive devices can be small and low-cost. Adaptation to different subject sizes is simply done in a straightforward manner, by positioning the subjects on a chair or other subject support as close as feasible to the scan center SC, or by standing as close as feasible to the scan center SC if no subject support is provided. The information about the angular subject position (e.g., angle α in FIG. 6) can be provided to the system by a handle 76 or other marker positioned in front of the patient. The angular range of the detector heads 12, 14 during imaging is the only other size adaptation, and this can be implemented entirely in software. The radiation detectors 12, 14 can be made small, and so the detectors are close to the subject so that spatial resolution and system efficiency are enhanced. Compared with existing cameras employing elliptical detector head orbits and a 2 cm subject-to-collimator distance, the close contact provided by the camera 10 is expected to provide 30% higher system efficiency at the same spatial resolution, as averaged for small and large patients $S_S$, $S_{XL}$. Having the subject in a sitting or standing position and using small detector heads enables the camera 10 to have a small footprint. The optimized data acquisition employing independent detector head movement discussed with reference to FIGS. 2-4 is readily employed in conjunction with the passively constrained detector head movement constrained by the passive constraints R1, R2, T1, T2. Either angular step-and-shoot acquisition or continuous list-mode acquisition can be used with the passive constraint arrangement. Conventional reconstruction techniques can be employed in conjunction with conventional parallel-hole collimators. The combination of relatively small Anger detector heads 12, 14 and low-cost passive constraints such as cams, rollers, ball bearings, tracks, grooves, or so forth provide a low cost system. The camera 10 is also readily used in conjunction with CZT or SiPM-based SPECT detectors since the active detector area can be small, e.g. 30 cm×20 cm. Such detectors can be made smaller than Anger cameras, to further reduce size. The camera 10 is optionally constructed as a moveable device, for example on wheels or rollers, enabling the camera 10 to be moved to the subject in an intensive care, trauma centre, emergency room, or other setting in which critically ill patients may be imaged.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A gamma camera comprising:
   at least two detector heads; and
   a gantry configured to move the at least two detector heads along a detector head path and to (i) acquire imaging data using the at least two detector heads, and (ii) during the acquisition of imaging data, move the two or more detector heads at independently controlled variable speeds or independently controlled data acquisition dwell times.

2. The gamma camera as set forth in claim 1 wherein the detector head path is generally elliptical, and the gantry includes at least an exterior elliptical wall substantially conforming with both the elliptical path and with a human torso.

3. The gamma camera as set forth in claim 1, further including:
   a controller configured to control the gamma camera to acquire imaging data while independently moving each detector head using an instantaneous speed or data acquisition dwell times optimized respective to an expected radioactive emission profile of a region of interest of a subject that is less than the entire subject; and
   an iterative reconstruction processor configured to iteratively reconstruct the acquired imaging data to generate a reconstructed image of at least the region of interest.

4. The gamma camera as set forth in claim 2, further including:
   passive constraints that constrain the at least two detector heads along the path with radiation-sensitive faces of the at least two detector heads continually generally facing a region of interest.

5. A gamma camera comprising:
   one or more detector heads;
   a gantry configured to move the one or more detector heads along a detector head path at controllable variable speed or controllable data acquisition dwell times;
   passive constraints that constrain the one or more detector heads along the path with radiation-sensitive faces of the one or more detector heads continually generally facing a region of interest; and
   a single motor per detector head independently driving each detector head along the detector head path.

6. The gamma camera as set forth in claim 5, wherein the gantry includes:
   a conformal wall contacting a subject to be imaged by the gamma camera, the one or more detector heads being in contact with an interior of the conformal wall wherein the interior of the conformal wall serves as one of the passive constraints that constrain the one or more detector heads along the path with radiation-sensitive faces of the one or more detector heads continually generally facing a region of interest.

7. The gamma camera as set forth in claim 5, wherein the detector head path is non-circular and non-semi-circular, and has an isocenter substantially coinciding with a region of interest positioned offset from an isocenter of a subject containing the region of interest.

8. The gamma camera as set forth in claim 7, wherein the subject is a human subject, and the region of interest is a heart of the subject.

9. The gamma camera as set forth in claim 4, wherein each passive constraint comprises a camming surface, a groove, a guide, or a track engaging the at least two detector heads.

10. The gamma camera as set forth in claim 5, wherein each passive constraint comprises a camming surface, a groove, a guide, or a track engaging the one or more detector heads.

11. The gamma camera as set forth in claim 5, wherein the one or more detector heads includes at least two detector heads.

\* \* \* \* \*